US012688915B2

(12) United States Patent (10) Patent No.: US 12,688,915 B2
Nishimoto et al. (45) Date of Patent: Jul. 21, 2026

(54) LIFE PLAN PROPOSAL DEVICE, LIFE PLAN PROPOSAL METHOD, AND PROGRAM STORAGE MEDIUM

(71) Applicant: NEC Corporation, Tokyo (JP)

(72) Inventors: Shinnosuke Nishimoto, Tokyo (JP); Kenichi Ueda, Tokyo (JP); Tsuyoshi Nakamura, Tokyo (JP); Yuki Kobayashi, Tokyo (JP); Genki Kusano, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 18/953,342

(22) Filed: Nov. 20, 2024

(65) Prior Publication Data

US 2025/0201369 A1 Jun. 19, 2025

(30) Foreign Application Priority Data

Dec. 15, 2023 (JP) ................................. 2023-212052

(51) Int. Cl.
*G16H 20/00* (2018.01)
*G16H 50/20* (2018.01)
*G16H 50/70* (2018.01)

(52) U.S. Cl.
CPC ............. *G16H 20/00* (2018.01); *G16H 50/20* (2018.01); *G16H 50/70* (2018.01)

(58) Field of Classification Search
CPC ........ G16H 20/00; G16H 50/20; G16H 50/70; G16H 20/70; G06N 20/00; G06F 40/56; G06Q 10/109
USPC ......................................................... 705/2, 3
See application file for complete search history.

(56) References Cited

U.S. PATENT DOCUMENTS

2012/0016817 A1* 1/2012 Smith ...................... G06N 5/02
706/46
2025/0014577 A1* 1/2025 Takahashi ............... G06F 3/167

FOREIGN PATENT DOCUMENTS

WO 2023/112745 A1 6/2023

* cited by examiner

*Primary Examiner* — Joshua B Blanchette
(74) *Attorney, Agent, or Firm* — Sughrue Mion, PLLC

(57) ABSTRACT

An acquisition unit of a life plan proposal device acquires attribute information indicating a user and living condition information relevant to a living condition of the user. An expansion unit adds additional attribute information of the user by an information generation method using the acquired attribute information. An estimation unit estimates a life event that is likely to happen in the user's life and a time of the life event by using the attribute information including the added attribute information, and the living condition information of the user. An output unit outputs a life plan generated by using information of the estimated life event.

8 Claims, 14 Drawing Sheets

| USER ID | TRANSACTION ID | PRODUCT ID | PRODUCT NAME | PURCHASE DATE |
|---------|----------------|------------|--------------|---------------|
| A | 1 | A | APPLE | 2023/1/5 |
| A | 2 | B | BANANA | 2023/1/6 |
| A | 3 | C | CARROT | 2023/1/7 |
| B | 4 | B | BANANA | 2023/1/5 |
| B | 5 | D | DOUGHNUT | 2023/1/6 |
| B | 6 | E | EGG | 2023/1/7 |
| C | 7 | A | APPLE | 2023/1/5 |
| C | 8 | D | DOUGHNUT | 2023/1/6 |
| C | 9 | F | FRENCH FRIES | 2023/1/7 |

Fig.5

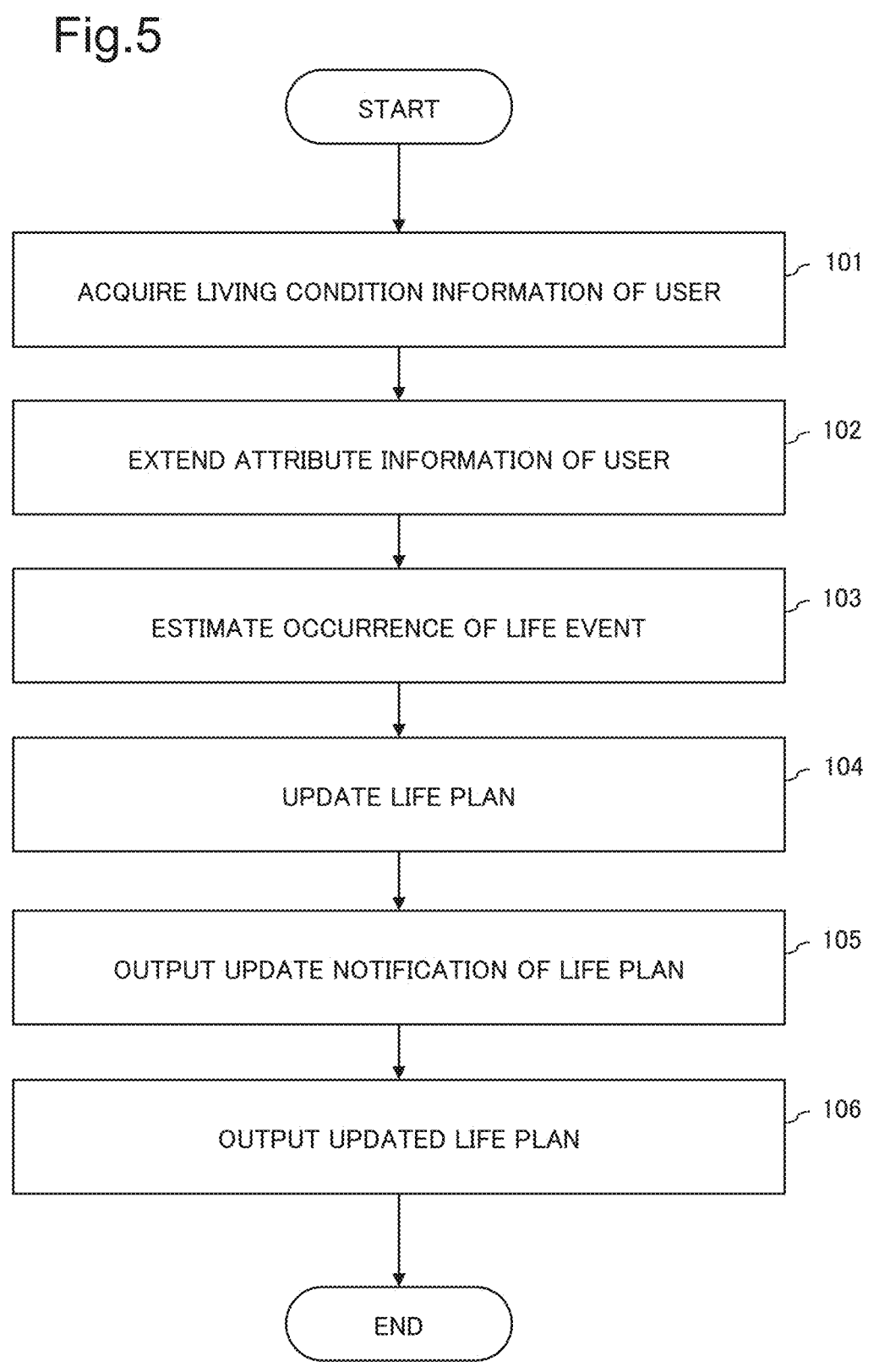

```
                    ┌─────────────┐
                    │    START    │
                    └─────────────┘
                           │
                           ▼
   ┌──────────────────────────────────────────────────┐
   │  ACQUIRE LIVING CONDITION INFORMATION OF USER      │──── 101
   └──────────────────────────────────────────────────┘
                           │
                           ▼
   ┌──────────────────────────────────────────────────┐
   │  EXTEND ATTRIBUTE INFORMATION OF USER              │──── 102
   └──────────────────────────────────────────────────┘
                           │
                           ▼
   ┌──────────────────────────────────────────────────┐
   │  ESTIMATE OCCURRENCE OF LIFE EVENT                 │──── 103
   └──────────────────────────────────────────────────┘
                           │
                           ▼
   ┌──────────────────────────────────────────────────┐
   │  UPDATE LIFE PLAN                                  │──── 104
   └──────────────────────────────────────────────────┘
                           │
                           ▼
   ┌──────────────────────────────────────────────────┐
   │  OUTPUT UPDATE NOTIFICATION OF LIFE PLAN           │──── 105
   └──────────────────────────────────────────────────┘
                           │
                           ▼
   ┌──────────────────────────────────────────────────┐
   │  OUTPUT UPDATED LIFE PLAN                          │──── 106
   └──────────────────────────────────────────────────┘
                           │
                           ▼
                    ┌─────────────┐
                    │     END     │
                    └─────────────┘
```

Fig.11

Fig.12
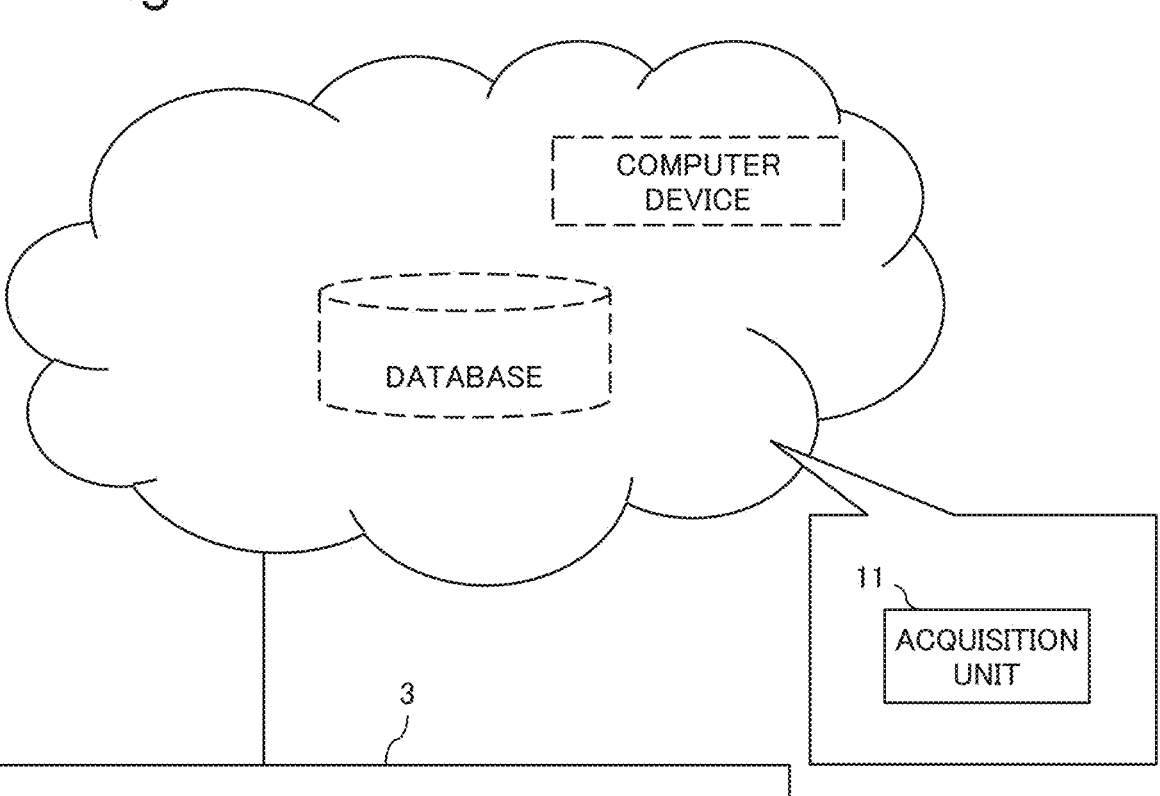
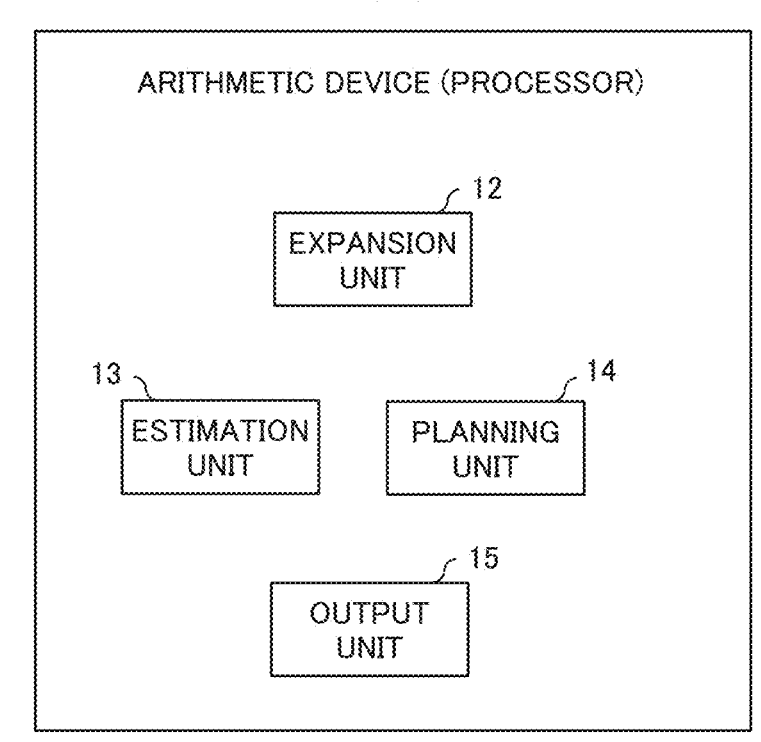

LIFE PLAN PROPOSAL DEVICE, LIFE PLAN PROPOSAL METHOD, AND PROGRAM STORAGE MEDIUM

This application is based upon and claims the benefit of priority from Japanese Patent Application No. 2023-212052, filed on Dec. 15, 2023, the disclosure of which is incorporated herein in its entirety by reference.

TECHNICAL FIELD

The present disclosure relates to a technology of proposing a life plan.

BACKGROUND ART

Reference 1 (WO 2023/112745 A1) discloses a technology of generating a future plan of a user. In the technology described in WO 2023/112745 A, future plan information of the user is generated based on basic information of the user and an ideal future plan, and the future plan information of the user is corrected in accordance with the reaction of the user who has seen the future plan information.

However, it is common that a future event predicted by the user when making the future plan happens at a timing deviated from the prediction even in a case where the timing is predicted. For this reason, even in a case where the future plan of the user is made, the future plan of the user often deviates from the current state due to the fact that the timing of the event predicted to happen deviates from the prediction, which makes the future plan of the user useless.

SUMMARY

A main object of the present disclosure is to provide a technology of proposing a future plan of a user matching the current state of the user even without information relevant to the future plan from the user.

As one aspect, a life plan proposal device of the present disclosure is a life plan proposal device, including: a memory configured to store instructions; and at least one processor configured to execute the instructions to: acquire attribute information indicating a user and living condition information relevant to a living condition of the user; add additional attribute information of the user by an information generation method using the acquired attribute information; estimate a life event that is likely to happen in the user's life and a time of the life event by using the attribute information including the added attribute information, and the living condition information of the user; and output a life plan generated by using information of the estimated life event.

As one aspect, a life plan proposal method of the present disclosure is a life plan proposal method, including: acquiring attribute information indicating a user and living condition information relevant to a living condition of the user; adding additional attribute information of the user by an information generation method using the acquired attribute information; estimating a life event that is likely to happen in the user's life and a time of the life event by using the attribute information including the added attribute information, and the living condition information of the user; and outputting a life plan generated by using information of the estimated life event, by a computer.

As one aspect, a non-transitory computer readable program storage medium of the present disclosure is a non-transitory computer readable program storage medium storing a computer program for causing a computer to execute: acquiring attribute information indicating a user and living condition information relevant to a living condition of the user; adding additional attribute information of the user by an information generation method using the acquired attribute information; estimating a life event that is likely to happen in the user's life and a time of the life event by using the attribute information including the added attribute information, and the living condition information of the user; and outputting a life plan generated by using information of the estimated life event.

BRIEF DESCRIPTION OF THE DRAWINGS

Exemplary features and advantages of the present invention will become apparent from the following detailed description when taken with the accompanying drawings in which:

FIG. 1 is a diagram illustrating an example embodiment of a life plan proposal device according to the present disclosure;

FIG. 2 is a diagram illustrating an example of information acquired by an acquisition unit;

FIG. 5 is a flowchart illustrating an operation example of the life plan proposal device;

FIG. 11 is a diagram illustrating an example of the life plan proposal system;

FIG. 12 is a diagram illustrating an example of the life plan proposal system;

EXAMPLE EMBODIMENT

Figure 3:
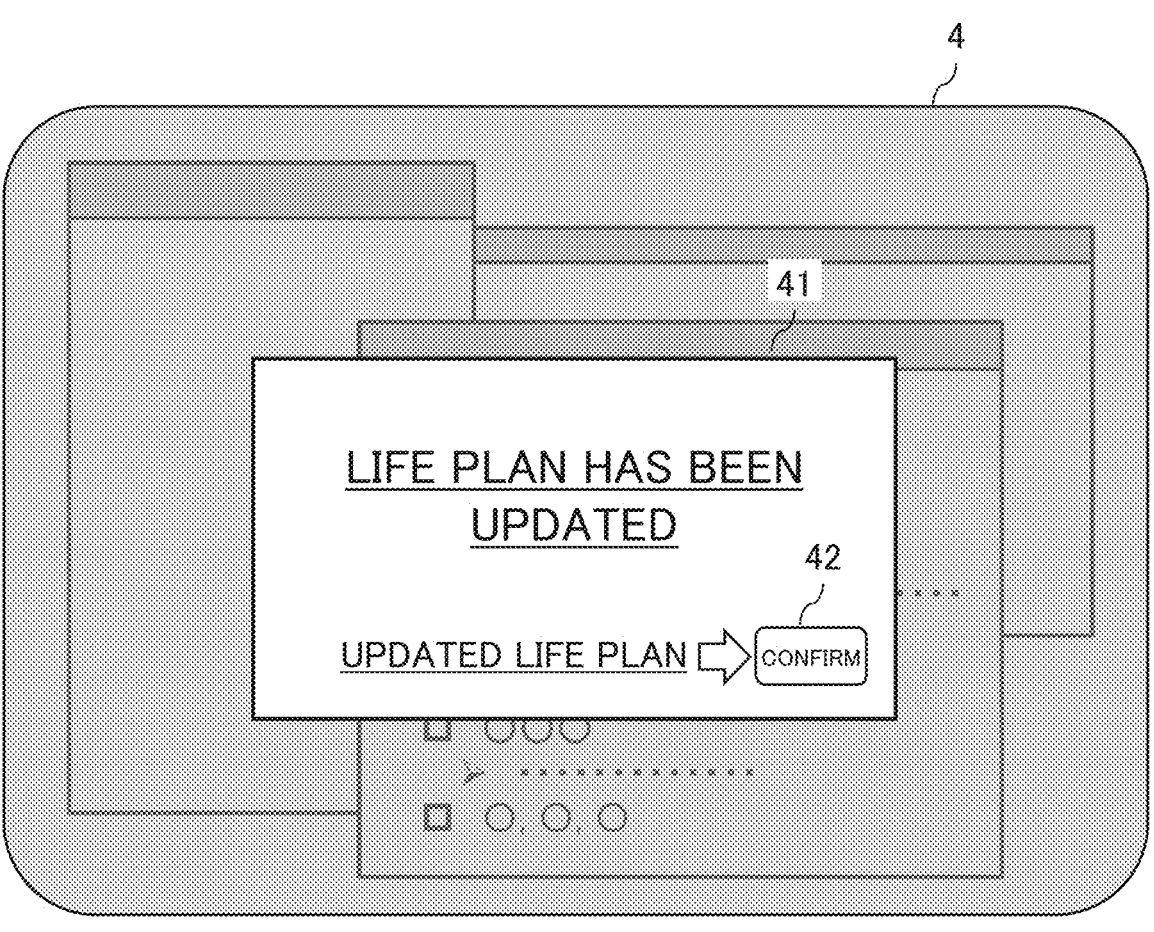
FIG. 3 is a diagram illustrating an example of a display mode for notifying an update notification.

Hereinafter, example embodiments of the present disclosure will be described with reference to the drawings.

First Example Embodiment

Definition and Application Example of Life Plan

In order to facilitate understanding of a first example embodiment, the definition of a life plan will be described. The life plan refers to an individual goal or dream in life, and a process of making a plan to achieve the goal or dream. This process includes various aspects of life, such as a financial plan, a career goal, family planning, and a retirement plan. Goal setting is a specific goal or desire that an individual wants to achieve, and a plan indicates a stepwise step or method for achieving such goals. In a time frame, a time for achieving the goal is set, and resource management is related to securing and managing necessary resources (money, time, skill, and the like).

An example of career planning includes a specific action plan, such as participation in training to improve skills and improvement in performance, by aiming at a promotion to manager by the age of 40. In the financial plan, a goal of purchasing the own house by the age of 35 is set, and the plan is advanced through monthly saving, investment, the selection of a housing loan, and the like. In the family planning, by aiming at having two children, the preparation of funds required for raising children, planning for childcare leave, saving for educational expenses, and the like are performed. In the retirement plan, by aiming at a retirement at the age of 60 and a life of enjoying hobbies and travels thereafter, the focus is on the calculation of a retirement allowance, investment in hobbies, and health management.

A financial institution provides financial services and advice suitable for customers by utilizing an individual life plan. By understanding the life plan of the customer, the financial institution is capable of performing a savings plan, an investment strategy, a proposal for a loan, the selection of an insurance product, and the like according to the needs of the customer.

For example, an educational loan or an investment product for improving the career is proposed to a customer who wants to develop the career. A customer planning to purchase a house is provided with options for a housing loan and a savings plan for purchasing a house. In the case of family planning focusing on educational expenses for children, a savings account for educational funds and an educational insurance are proposed.

Device Configuration

A life plan proposal device according to the first example embodiment is a computer device that provides a life plan proposal service, and generates and updates a life plan to propose a life plan suitable for the current state of a user. In addition, the life plan proposal device of the first example embodiment has a function of proposing the updated life plan suitable for the current state of the user even in a case where update information is not provided from the user.

Figure 1:
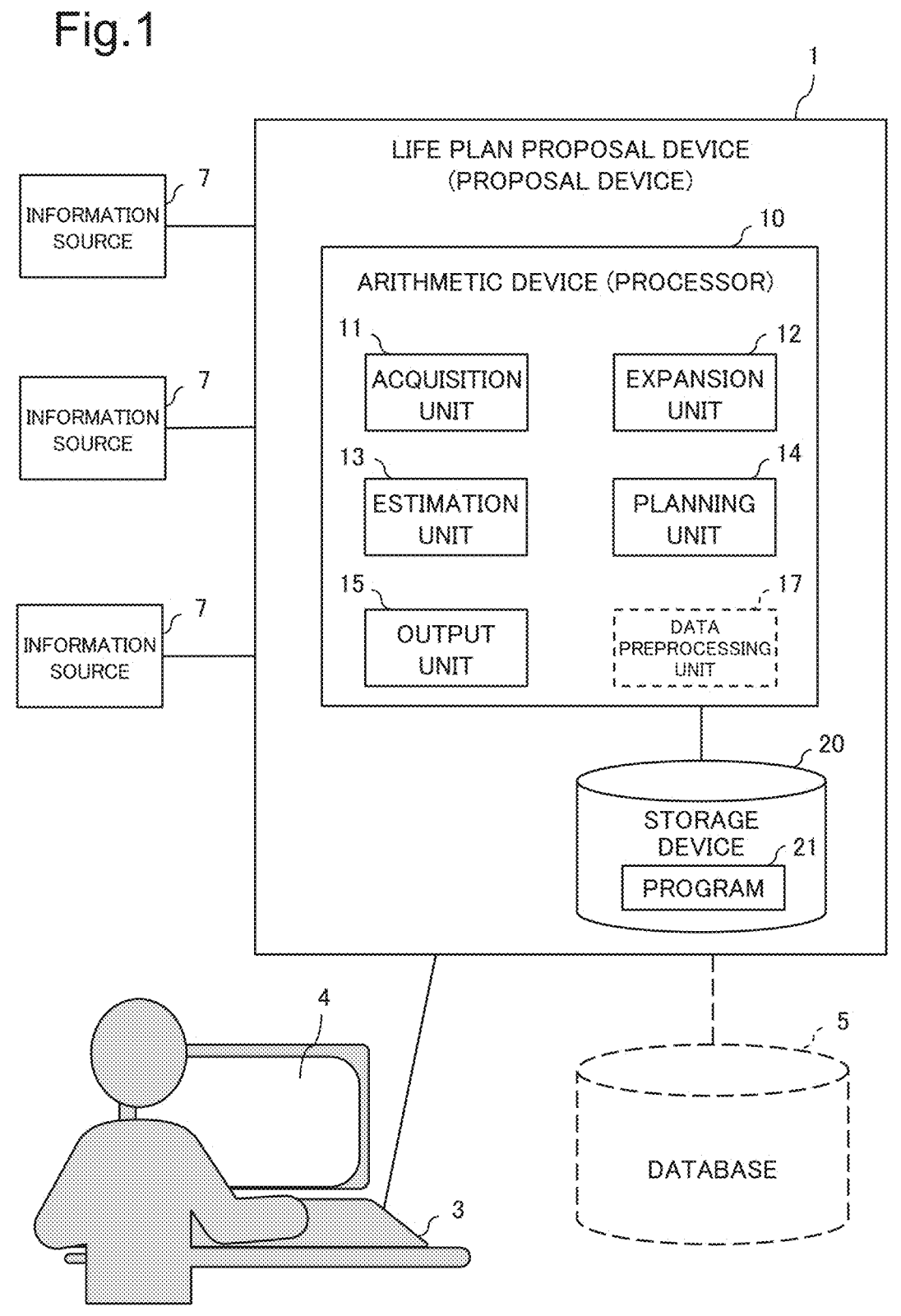

That is, a life plan proposal device (hereinafter, simply referred to as a proposal device) 1 of the first example embodiment has, for example, a configuration as illustrated in FIG. 1, and is connected to a terminal device 3. The terminal device 3 is, for example, an information device manipulated by the user using the life plan proposal service by the proposal device 1, and includes a communication function and a display control function.

The communication function is a function of communicating information with other devices with a communication function through an information communication network such as the Internet. The display control function is a function of displaying information on a display device 4 by controlling the display operation of the display device 4. The type of terminal device 3 is not limited as long as the terminal device 3 is an information device having such a communication function and a display control function, and specific examples of the terminal device include a smart phone, a tablet, and a personal computer. When the terminal device 3 is a smart phone or a tablet, the display device 4 is integrated with the terminal device 3, but when the terminal device 3 is a personal computer, the display device may be externally attached. In the example of FIG. 1, the number of terminal devices 3 connected to the proposal device 1 is one, but the number of terminal devices 3 connected to the proposal device 1 is not limited, and there may be a plurality of terminal devices. Even when a plurality of terminal devices 3 are connected to the proposal device 1, the proposal device 1 carries out the same function on each of the terminal devices 3, and thus, here, the description of a case where the plurality of terminal devices 3 are connected will be omitted.

The terminal device 3 is cooperated with the proposal device 1 through information exchange with the proposal device 1 by an application program (an application) or a browser (software for browsing information on the Internet) for providing a cooperation function with the proposal device 1. By which of the application and the browser the cooperation between the terminal device 3 and the proposal device 1 is executed is suitably set by a designer or the like, and is not limited here.

The proposal device 1 is also connected to an information source 7. The information source 7 is an information source that is capable of providing the proposal device 1 with information used for life plan generation processing and update processing executed by the proposal device 1. The number of information sources 7 connected to the proposal device 1 and a connection destination as the information source 7 are suitably set, for example, by the designer of the proposal device 1, in consideration of the processing content of the proposal device 1. However, here, at least the information source 7 that is capable of providing the living condition information of the user to the proposal device 1 is included as one of the information sources 7.

The living condition information of the user is information relevant to the living condition of the user. For example, specific examples of the living condition information include purchase history information, history information of a search keyword on a search site, browsing history information of a website, trajectory information of position information of a mobile terminal, communication history information of a terminal device, purchase history information of a ticket, billing history information, and the like. The purchase history information of the user includes a credit card usage history, an electronic commerce (EC) site usage history, and the like. The purchase history information of the ticket includes a purchase history of a ticket for an event such as a concert, a purchase history of a ticket (a so-called ticket) for using a transport such as a train or an airplane, and the like. The billing history information is, for example, information of a user billing history in a service by an application program provided through the Internet.

Another example of the living condition information includes information of a post content posted by the user on a social networking service (SNS) or the like, information relevant to the physical condition of the user, such as a medicine history (a dispensing history) or hospital visit information of the user, schedule information, and the like. Examples of the schedule information include schedule information retained in a terminal device of the user, schedule information managed by a business operator providing a schedule management service, and the like.

As described above, there are various types of living condition information of the user. In other words, such living condition information is information indicating the action content of the user, and the living condition information includes information of time (a time or a date) when the user acts. In a case where there is information such as the schedule information retained in the terminal device of the user as the living condition information used for the processing by the proposal device 1, the terminal device of the user is set as the information source 7.

As the information source 7, an information source that is capable of providing living environment information indicating the living environment of the user, such as information on the family of the user, information on an income, and information indicating the occupation of the user, to the proposal device 1 may be set. Since the living environment of the user affects the living condition of the user, the living environment information of the user is considered to be included in the living condition information of the user. However, the living environment information is not information indicating the action content of the user, and may not include time information.

The proposal device 1 includes an arithmetic device 10 and a storage device 20. The storage device 20 includes a computer readable program storage medium that stores data and a computer program (hereinafter, also referred to as a program) 21. There are a plurality of types of storage devices such as a magnetic disk device and a semiconductor memory element, and there are a plurality of types of semiconductor memory elements such as a random access memory (RAM) and a read only memory (ROM). The computer device includes a plurality of types of storage devices according to the usage, and such storage devices are collectively referred to as the storage device 20 without distinguishing the storage devices from each other. The type and number of storage devices 20 included in the proposal device 1 are not limited, and the description of the type and number of storage devices will be omitted. The proposal device 1 may be connected to a database 5 that is a storage device. In this case, the proposal device 1 may write information to the database 5 or read information from the database 5, but in order to avoid the complication of the description, the description of such a case will be omitted here.

The arithmetic device 10 includes a processor such as a central processing unit (CPU) and a graphics processing unit (GPU). The arithmetic device 10 may have a function based on the program 21 by reading and executing the program 21 stored in the storage device 20. Here, the arithmetic device 10 includes an acquisition unit 11, an expansion unit 12, an estimation unit 13, a planning unit 14, and an output unit 15, as functional units according to the generation and the update of the life plan.

The acquisition unit 11 acquires attribute information and the living condition information of the user. The attribute information of the user is information indicating the user. Here, the attribute information of the user is information that can be also referred to as person information or profile information, and is, for example, information such as a name, an age, an address, and a revenue. The number and type of attribute information of the user acquired by the acquisition unit 11 are suitably set by the designer of the proposal device 1 or the like, in consideration of, for example, service contents provided by the proposal device 1.

Here, a method by which the acquisition unit 11 acquires the attribute information of the user is not limited, but as an example, there is a method for acquiring the attribute information from the user in cooperation with the terminal device 3. For example, a screen for inputting the attribute information is displayed on the display device 4 of the terminal device 3 by the cooperation between the proposal device 1 (the acquisition unit 11) and the terminal device 3, and in a case where the user inputs the attribute information on a display screen, the input attribute information is transmitted from the terminal device 3 to the proposal device 1.

The acquisition unit 11 acquires the attribute information of the user by receiving the transmitted attribute information.

As the display mode of the screen for inputting the attribute information of the user displayed on the display device 4, a suitable display mode considering, for example, the explicitness of input items to which the user wants to input information can be adopted, but the display mode is not limited here, and thus, the description of the display mode will be omitted. In a case where the attribute information is acquired from the user as described above, a questionnaire for acquiring the information used for the life plan generation processing from the user may be further performed, and the acquisition unit 11 may acquire an answer to the questionnaire. Such an answer to the questionnaire may also be used as the attribute information of the user.

Instead of acquiring the attribute information from the user, for example, the acquisition unit 11 may acquire the attribute information of the user from the information source 7. In this case, for example, a computer device that manages the attribute information of the user is set as the information source 7 to which the acquisition unit 11 is connected. An example of the computer device is a computer device that controls an administrative system (for example, Mynaportal) supporting search for an administrative procedure such as child care and nursing care, and online application.

The acquisition unit 11 stores the acquired attribute information of the user in the storage device 20 in association with identification information of the user (hereinafter, also referred to as user identification information). An example of a timing when the acquisition unit 11 acquires the attribute information of the user as described above is when the user starts to receive the life plan proposal service by the proposal device 1.

The acquisition unit 11 further acquires the living condition information of the user. As described above, the living condition information of the user is information indicating the living condition of the user. The acquisition unit 11 acquires the living condition information of the user from the information source 7 at a timing set in advance. The timing when the acquisition unit 11 acquires the living condition information from the information source 7 may be suitably set in accordance with the type of living condition information, but is not limited, and may be, for example, at a time interval (once a month or the like) set in advance. In a case where an update notification indicating that the living condition information of the user has been updated is set to be transmitted from the information source 7 to the proposal device 1, the acquisition unit 11 may acquire the updated living condition information from the information source 7 upon receiving the update notification. That is, as the timing when the acquisition unit 11 acquires the living condition information from the information source 7, a timing when the update notification is received from the information source 7 may be set.

The acquisition unit 11 stores the acquired living condition information of the user in the storage device 20 in association with the identification information of the user (the user identification information).

However, in a case where the acquisition unit 11 acquires the attribute information and the living condition information of the user from the information source 7, there are a case where information related to an individual user can be acquired from the information source 7 and a case where the acquisition unit 11 collectively acquires information related to a plurality of users from the information source 7. In a case where the information related to the plurality of users is collectively acquired from the information source 7, for example, the information of each of the users is acquired as follows.

For example, it is assumed that the information related to the plurality of users as illustrated in FIG. 2 is acquired from the information source 7 as a collection of information. The information illustrated in the example of FIG. 2 is purchase information (living condition information) of a customer in a certain store. In this example, information such as a transaction identification (ID) for identifying transaction data, a user ID for identifying a customer (a user), a product ID for identifying a purchased product, a product name of the purchased product, and a purchase date is associated with each transaction data.

Such a plurality of pieces of information (transaction data) is clustered (grouped) by a clustering technology such as K-means or hierarchical clustering. Then, by analyzing a feature such as a purchase pattern for each cluster (group), a feature of each user is obtained, and the feature is acquired as the living condition information of the user. As a specific example of the living condition information in this case, living condition information such as "in January 2023, a user A exhibits a health-conscious purchasing behavior, a user B purchases food in a well-balanced manner, and a user C tends to prefer sweets and fast food" is acquired. A method for extracting the living condition information of the user from the plurality of pieces of information including the information related to the plurality of users is not limited to the method described here, and other methods may be adopted.

The acquisition unit 11 may acquire the living condition information of the user by acquiring information disclosed as open data from one or a plurality of information sources 7 and extracting the living condition information of the user from the acquired information. Examples of a method for extracting the living condition information of the user from the open data as described above include a method for processing the open data by a database technology using information relevant to the user.

When the open data is processed by the database technology, the proposal device 1 may further include a data preprocessing unit 17 as indicated by a dotted line in FIG. 1. A technology in which the data preprocessing unit 17 adds the open data by the database technology will be described. For example, the data preprocessing unit 17 may process the open data by tagging text data with additional information or attributes using a machine learning model.

The data preprocessing unit 17 may perform data structuring, meaning prediction, and similarity evaluation using a natural language processing technology. As a result, text data and unstructured data may be converted into structured data.

The format (the data format) of the attribute information and the living condition information acquired by the acquisition unit 11 and stored in the storage device 20 is a format that can be easily processed by the functional units such as the expansion unit 12 and the estimation unit 13.

By using the attribute information of the user acquired by the acquisition unit 11, the expansion unit 12 adds the additional attribute information of the user by an information generation method. Here, the information generation method is a technology for estimating the attribute information to increase the attribute information. As an example of the information generation method, there is a method using an attribute information database. In the attribute information database, a plurality of pieces of information that can be the attribute information are stored in association with each other. In the case of using the attribute information database, for example, the expansion unit 12 searches the attribute information database for information related to the attribute information of the user acquired by the acquisition unit 11. When the information related to the attribute information of the user is found in the attribute information database by the search, the expansion unit 12 reads information associated with the found information from the attribute information database as the estimated attribute information of the user. Then, the expansion unit 12 adds the information read from the attribute information database to the attribute information of the user as the additional attribute information of the user. That is, the expansion unit 12 stores the additional attribute information of the user in the storage device 20 in association with the user identification information, similarly to the other attribute information.

As another example of the information generation method, there is a method using a language model based on an AI technology. The language model here is a language model learned by a machine learning algorithm for the attribute information, and is capable of outputting the estimated additional attribute information in response to the input of a query with contents for requesting the additional attribute information. When such a language model is used, the expansion unit 12 generates the attribute information and adds (extends) the attribute information as follows.

For example, as a template for a query to be input to the language model, a query (a sentence) "what is the attribute of the user associated with {attribute}?" is given in advance. The attribute information of the user is input to {attribute} in the template. More specifically, it is assumed that occupation information such as an engineer is acquired by the acquisition unit 11 as one of the attribute information of the user and stored in the storage device 20. The expansion unit 12 reads, for example, the occupation information "engineer" that is the attribute information of the user from the storage device 20, and inputs the read attribute information to {attribute} of the template for the query, thereby generating a query "what is the attribute of the user associated with the engineer" as input information to the language model. The expansion unit 12 inputs the generated query to the language model, and acquires output information from the language model according to the query as the additional attribute information estimated by the language model. Specifically, for example, in response to the input of the query "what is the attribute of the user associated with the engineer?", the language model outputs (answers) information such as "programming", "software development", and "system design". The expansion unit 12 stores, that is, adds, as the additional attribute information estimated by the language model, the information output from the language model in the storage device 20 in association with the user identification information of the user whose attribute information is to be added. In a case where a plurality of pieces of attribute information is stored in the storage device 20 as the attribute information, the expansion unit 12 executes the same information generation processing relevant to the addition of the attribute while sequentially changing the attribute information.

The language model calculates the appearance probability of a word (the attribute information) relevant to the query that is the input information, and outputs the word (the attribute information) having a high appearance probability (for example, an appearance probability equal to or more than a threshold value) as the additional attribute information. Therefore, the additional attribute information output from the language model is not limited to one, and there may be a plurality of pieces of additional attribute information as in the specific example described above. Even in a case where the same query is input to the same language model, the output from the language model is not necessarily the same. Using this, for example, the expansion unit 12 may acquire the additional attribute information that is a plurality of different pieces of output information by repeatedly inputting the same query to the same language model. The language model used by the expansion unit 12 may be set in such a way as to also output information of the appearance probability associated with the additional attribute information as the output information.

The above-described information generation method is an example, and the information generation method used by the expansion unit 12 is not limited to the above-described information generation method as long as it is a technology capable of adding (extending) the additional attribute information using the acquired attribute information.

Using the attribute information including the attribute information added by the information generation processing as described above, the expansion unit 12 repeatedly executes extension processing of the attribute information at each timing set in advance. By such processing of the expansion unit 12, the attribute information of the user increases.

The estimation unit 13 estimates a life event that is likely to happen in the user's life and a time of the life event by using the attribute information and the living condition information of the user including the added attribute information. The life event is an event in which the living condition is considered to greatly change in life, and specific examples of the life event include marriage, child birth, child's school entrance, serious illness, and career change. A moving house, a purchase of a car or a house, and the like may also be included in the life event.

There are various methods for estimating the life event that is likely to happen in the user's life (likely to be experienced to the user) and a time of the life event using the attribute information and the living condition information of the user. For example, as an example, there is a method using a language model. In this method, for example, the living condition information (such as a purchase history, a search keyword, and a word or a phrase (a sentence) as a search result) of the user is learned by the language model. Then, a query for asking the life event that is likely to happen in the user's life is input to the language model, so that information indicating the life event that is likely to happen is output from the language model as an estimation result. The time of the life event that is likely to happen is estimated by analyzing the living condition information of the user focusing on a term or the like relevant to the life event. By such estimation processing, for example, an estimation result indicating that the life event such as career change is likely to happen within several months is output from the estimation unit 13.

As an example of another estimation method, there is a method using a classification model based on an AI technology. In such an estimation method, for example, a plurality of life events are classified into a group that the user is likely to experience and a group that the user is not likely to experience by using a plurality of pieces of information (Information such as an age, a purchase history, and a search keyword history (in other words, a feature)) selected from the attribute information and the living condition information of the user. For the life event of the group that the user is likely to experience, whether the time (an experience time) is close (for example, whether it is within one year) is determined by using the living condition information of the user, and the time is speculated (estimated) such that the time (the experience time) is estimated when the life event is close.

As another estimation method of the life event, there is a method using a clustering technology. In such a method, for example, a plurality of users are clustered by using, for example, information of a purchase history or a website browsing history, which is the living condition information of the user, and a group of users performing similar purchase behavior or website browsing behavior is generated. Then, a life event that is likely to happen (likely to be experienced) commonly to the user is estimated for each group. For the life event estimated to be likely to happen, the speculation (the estimation) of the time is performed such that the time (the experience time) is estimated by using the living condition information for each user.

As another estimation method of the life event, there is a rule-based method. In such a method, for example, information of a relevant term is given as an event-relevant term for each life event. Then, it is determined whether a term related to the event-relevant term is included in the text data included in the living condition information (the purchase history, the website browsing history, or the like) of the user. Accordingly, in a case where the term related to the event-relevant term is included, it is estimated that the time of the life event relevant to the included event-relevant term is close. For the life event estimated to be about to happen, the speculation (the estimation) of the time is performed such that the time is estimated by using the living condition information.

As another estimation method of the life event, there is a method using the number of terms extracted from the text data included in the living condition information of the user. In such a method, for example, as described above, the information of the relevant term is given as the event-relevant term for each life event. Then, in a case where there is the term related to the event-relevant term among the terms extracted from the text data included in the living condition information of the user, the number of appearances of the term is counted. A life event relevant to a term of which the count number is equal to or more than a threshold value is estimated as an event of which the time is close. For the life event estimated to be about to happen, the speculation (the estimation) of the time is performed such that the time is estimated by using the living condition information.

As another estimation method of the life event, for example, there is a method for analyzing chronological data acquired as the living condition information of the user. In such a method, for example, by analyzing the chronological data acquired as the living condition information of the user, in a case where it is detected that the number of appearances of the event-relevant term included in the chronological data rapidly increases, the life event relevant to the detected event-relevant term is estimated as the event of which the time is close. For the life event estimated to be about to happen, the speculation (the estimation) of the time is performed such that the time is estimated by using the living condition information.

As described above, there are various estimation methods for estimating the life event that is likely to happen in the user's life (likely to be experienced to the user) and the time of the life event. Here, the estimation method adopted by the estimation unit 13 is suitably set by the designer or the like of the proposal device 1 in consideration of the type and number of pieces of information acquired as the living condition information of the user, the number of users, and the like, and is not limited.

The estimation unit 13 may adopt a plurality of estimation methods and estimate the life event that is likely to happen in the user's life and the time of the life event by each of the estimation methods. As described above, in a case where the occurrence of the life event and the time of the life event are estimated by the plurality of estimation methods, for example, the certainty (the reliability) of the estimation result may differ depending on the type of estimation method. For this reason, for example, in a case where the occurrence of the life event and the time of the life event are estimated using each of the plurality of estimation methods, it is conceivable to associate information of the certainty (the reliability) of the estimation result with the estimation result (information indicating the life event estimated to be likely to happen and the estimated time of the life event).

In a case where the information of the appearance probability as described above is associated with the attribute information added to the expansion unit 12, the estimation unit 13 may determine whether to use the attribute information for the estimation processing by using the appearance probability and the contents of the living condition information.

The estimation unit 13 stores the estimation result by the above-described estimation processing in the storage device 20 in association with the user identification information of the related user. The information of the estimation result stored in the storage device 20 is associated with, for example, information of time when the estimation processing is executed.

For example, the planning unit 14 generates the life plan of the user by using the attribute information of the user when the generation of the life plan is requested from the terminal device 3 by the manipulation of the user. The life plan is lifetime living design, and is, for example, a life plan (a design drawing) in which the estimated time of the life event, the estimated transition situation of the revenue and expenditure, the transition of an asset situation, a change in a family structure, and the like are associated with age. Various forms of life plans are proposed, and there are various generation methods of the life plan. Here, since the form of the life plan and the generation method of the life plan are not limited, the description of the form and the generation method will be omitted. The type of attribute information acquired from the user is set in consideration of the information relevant to the user used in the life plan generation processing executed by the planning unit 14.

The planning unit 14 further updates (generates) the life plan of the user by using the information of the life event estimated by the estimation unit 13 at an update timing set in advance. The update timing here is, for example, a timing triggered by a result of such estimation in a case where the occurrence of the life event is estimated by the estimation unit 13 for each user. There is a case where the life event that is likely to happen is already incorporated in the life plan by the estimation unit 13. In such a case, for example, the estimated time of the life plan is compared with the time of the life plan reflected on the life plan, and a timing triggered by detecting that a deviation between the times exceeds an allowable range may be the update timing.

For each user at a time interval set in advance, it is determined whether there is a life event that is likely to happen during the time interval by the estimation unit 13, and a timing triggered by determining that there is the estimated life event may be the update timing.

That is, here, life plan update processing by the planning unit 14 is not performed in response to an update request from the user, but is executed in a case where the occurrence of a new life event of the user and the time of the new life event are estimated by the processing of each of the acquisition unit 11, the expansion unit 12, and the estimation unit 13.

Although a method for updating the life plan by the planning unit 14 is not limited here, for example, there is a method for regenerating the life plan by using the information of the life event estimated by the estimation unit 13, or updating the life plan with reference to the life plan of another user in which the time of the life event is similar.

In a case where the occurrence of a plurality of life events is estimated by the estimation unit 13, for example, the planning unit 14 updates the life plan by using the life event selected in accordance with a rule set in advance, among the plurality of estimated life events.

The life plan generated/updated by the planning unit 14 is stored in the storage device 20 in association with the user identification information of the user related to the life plan.

The output unit 15 outputs the life plan newly generated by the planning unit 14 and the updated life plan to the terminal device 3. That is, in a case where the planning unit 14 generates the life plan in response to a life plan generation request from the terminal device 3, the output unit 15 returns the generated life plan to the terminal device 3. In a case where an updated life plan provision request is transmitted from the terminal device 3 to the proposal device 1, the output unit 15 returns the updated life plan by the planning unit 14 to the terminal device 3 in response to the provision request. As described above, in a case where the output unit 15 outputs the life plan to the terminal device 3, the life plan is output in response to the request from the terminal device 3 (in other words, the user).

As described above, the life plan update processing by the planning unit 14 is not executed in response to the request from the user, but is executed in response to the results of the processing of the acquisition unit 11, the expansion unit 12, and the estimation unit 13. That is, the life plan update processing is performed without the recognition of the user. Therefore, as one of the functions, in a case where the updated life plan is generated by the planning unit 14, the output unit 15 outputs a notification (hereinafter, also referred to as an update notification) for notifying that the life plan has been updated toward the terminal device 3 of the user whose life plan has been updated. An output method of the update notification is not limited, and for example, there is a method using a communication means such as an electronic mail or a chat. As the output method of the update notification, there is also a method in which the update notification is output from the proposal device 1 to the terminal device 3 by a cooperative operation between the proposal device 1 (the output unit 15) and the terminal device 3.

When the update notification is output to the terminal device 3 by the cooperative operation between the proposal device 1 and the terminal device 3, the terminal device 3 notifies the user of the update notification as follows. For example, when the user manipulates the terminal device 3 for information search, document preparation, or the like, the display control function of the terminal device 3 causes a pop-up screen (a pop-up window) 41 to display the update notification of the life plan as illustrated in FIG. 3 on the display screen of the display device 4. For example, a confirmation icon 42 is displayed on the pop-up screen 41. The icon 42 includes address information of a connection destination connected to a web page for browsing the updated life plan. By using the icon 42, the user can display the web page for browsing the updated life plan on the screen of the display device 4.

Figure 4:
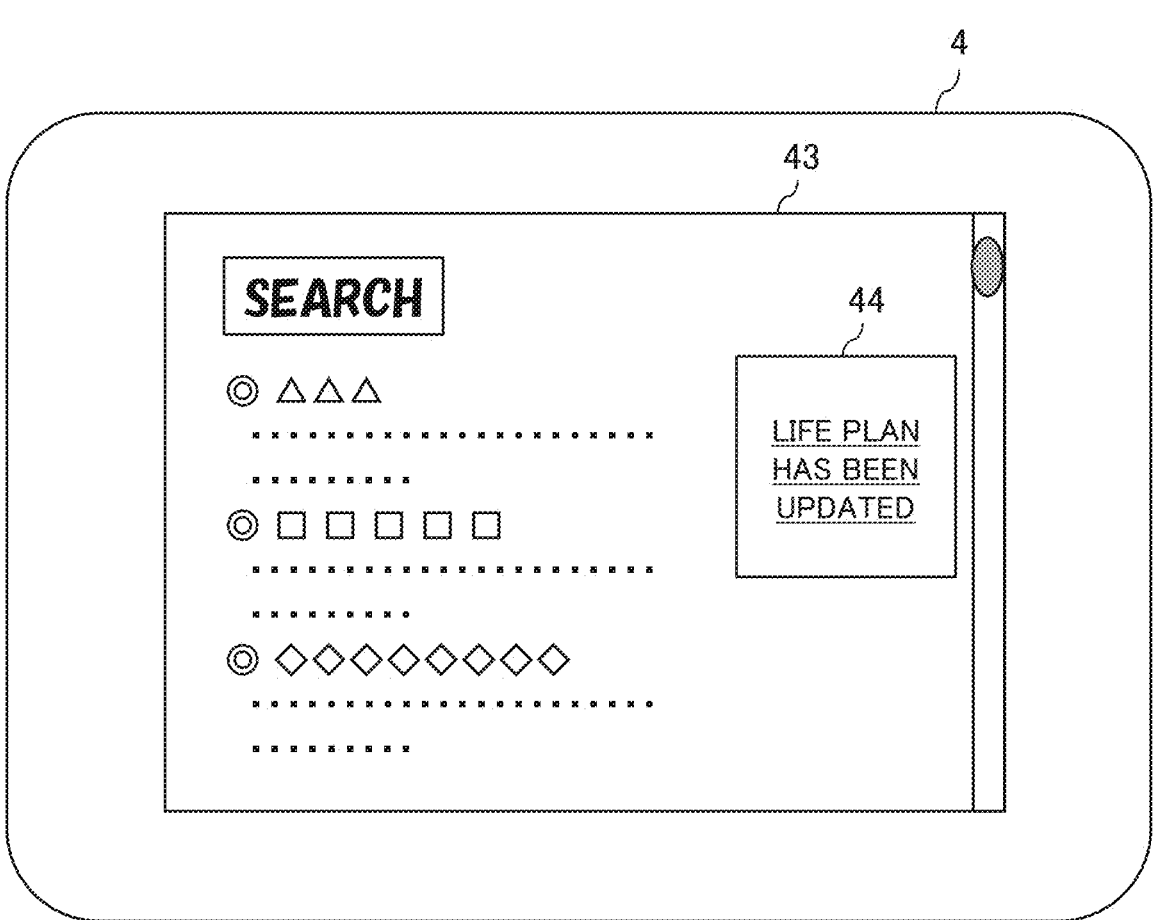
FIG. 4 is a diagram illustrating another example of the display mode for notifying the update notification.

As a method for notifying the user of the update notification, instead of using the pop-up screen, for example, the update notification may be displayed in a screen region 44 for an advertisement column on a screen 43 that displays the search result on the search site as illustrated in FIG. 4. In such a case, in order to prevent the user from overlooking the update notification, for example, a character display mode such as blinking the display of characters may be adopted.

Various timings are conceivable as a notification timing when the terminal device 3 notifies the user of the update notification of the life plan. Examples of the notification timing include a timing when the terminal device 3 receives the update notification of the life plan, a timing when a notification condition set in advance is satisfied after the update notification of the life plan is received, and the like. The notification condition is not limited, but as an example, there is a condition such as when browsing a web site relevant to the life event. The notification timing of the update notification of the life plan may be set in advance by the designer of the proposal device 1, or may be selected by the user among a plurality of notification timings set in advance by the designer of the proposal device 1.

The proposal device 1 of the first example embodiment is configured as described above. Next, an example of an operation according to the life plan proposal in the proposal device 1 will be described with reference to FIG. 5. FIG. 5 is a flowchart illustrating an example of the operation according to the life plan proposal in the proposal device 1. It can also be said that FIG. 5 is a diagram illustrating a life plan proposal method in the proposal device 1.

For example, in order to receive the life plan proposal service by the proposal device 1, it is assumed that the user registers the attribute information of the user oneself in the proposal device 1 by using the terminal device 3. In other words, it is assumed that the acquisition unit 11 acquires the attribute information from the user, and the acquired attribute information of the user is stored in the storage device 20. It is assumed that the planning unit 14 generates the life plan of the user by using the attribute information of the user, and the life plan is stored in the storage device 20 in association with the user identification information.

In such a case, for example, the acquisition unit 11 acquires the living condition information of the user at a timing set in advance (step 101 in FIG. 5). The expansion unit 12 extends (adds) the attribute information of the user by the information generation method using the attribute information of the user (step 102).

The estimation unit 13 estimates the life event that is likely to happen in the user's life and the time of the life event by using the living condition information acquired by the acquisition unit 11 and the attribute information including the attribute information added by the expansion unit 12 (step 103).

In a case where the occurrence of the life event and the time of the life event are estimated by the estimation unit 13, the planning unit 14 updates the life plan of the user by also using the information of the estimated life event (step 104). As a result, the output unit 15 outputs the update notification of the life plan to the terminal device 3 of the user (step 105).

Thereafter, for example, in a case where the updated life plan provision request is received from the terminal device 3, the output unit 15 outputs (returns) the updated life plan to the terminal device 3 in response to the request (step 106).

The proposal device 1 of the first example embodiment has the above-described configuration. That is, the proposal device 1 acquires the living condition information of the user by the acquisition unit 11, estimates the occurrence of the life event and the time of the life event from the living condition information by the estimation unit 13, and updates the life plan of the user by the planning unit 14 using the information of the occurrence of the estimated life event and the estimated time of the life event. With such a configuration, the proposal device 1 is capable of updating the life plan without acquiring additional information from the user and without receiving the update request from the user.

The proposal device 1 includes the expansion unit 12, and the attribute information of the user can be added by the expansion unit 12. That is, since the attribute information of the user used for the estimation processing of the life event by the estimation unit 13 can be increased, the type of information obtained from the estimation processing by the estimation unit 13 can be increased, or reliability relevant to the information can be enhanced. For example, it is assumed that the occupation information "engineer" is acquired as one piece of attribute information from the user, and the attribute information is not added by the expansion unit 12. In such a case, it is assumed that the estimation unit 13 obtains an estimation result (information) indicating that, for example, a life event "marriage", "career change", or "new house purchase" is likely to happen in the user's life within several months. On the other hands, it is assumed that, for example, attribute information "software development" is added by the expansion unit 12. As a result, it is conceivable that the estimation unit 13 suggests that the user who is interested in information technology (IT) and a technology plans a marriage in the near future, and further obtains an estimation result (information) that there is a high possibility that the user is interested in an innovative wedding-experience utilizing virtual reality (VR).

Other Example Embodiments

The present disclosure is not limited to the first example embodiment described above, and various example embodiments can be adopted. For example, in the first example embodiment, in the steps from when the occurrence of the life event is estimated by the estimation unit 13 to when the life plan is updated by the planning unit 14, the processing is executed without receiving information from the user. On the other hand, for example, the estimation unit 13 may perform processing of transmitting the estimation result to the terminal device 3 through the output unit 15 and causing the user to confirm the estimation result after estimating the occurrence of the life event. For example, it is assumed that results such as "a life event "marriage" will happen within several months", "a life event "career change" will happen within several months", and "a life event "new house purchase" will happen within several months to 1 year" are obtained as the estimation result by the estimation unit 13. The estimation unit 13 transmits such an estimation result to the terminal device 3 of the user, causes the display device 4 to display the estimation result, and causes the user to input information indicating whether the estimation result is correct. In other words, the estimation unit 13 causes the user to confirm the estimation result. When receiving a confirmation result by the user from the terminal device 3, the estimation unit 13 associates the received information with information of the related estimation result. In a case where the estimation result by the estimation unit 13 is presented to the user, and the estimation unit 13 calculates the certainty (the reliability) of the estimation result, the information of the certainty (the reliability) of the estimation result may also be presented.

In a case where the estimation result is confirmed by the user as described above, for example, the planning unit 14 updates the life plan by using the information of the life event confirmed to happen by the user.

Figure 6:
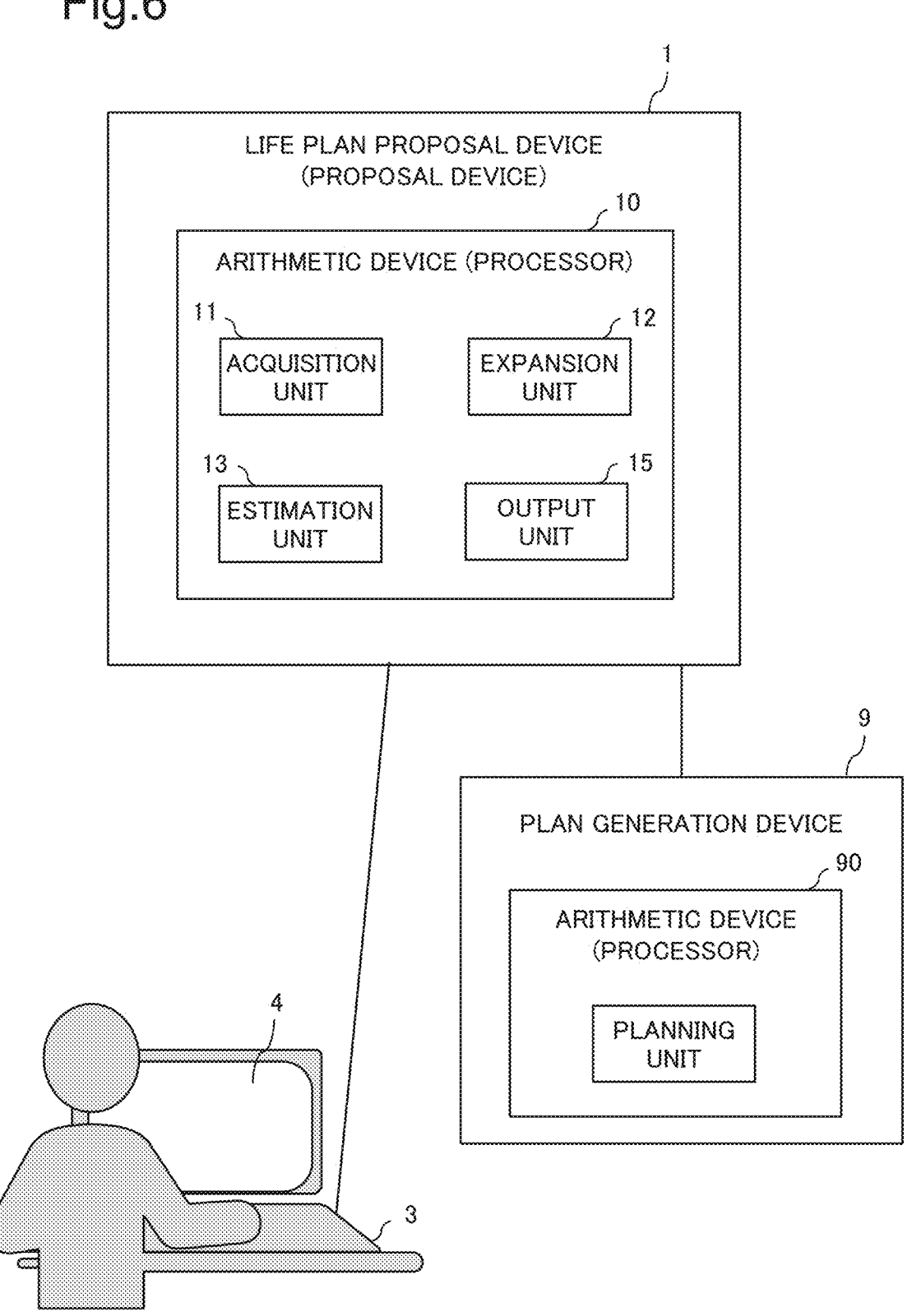
FIG. 6 is a diagram illustrating another example embodiment of the life plan proposal device.

The proposal device 1 of the first example embodiment includes the planning unit 14, but for example, in a case where a plan generation device 9 as illustrated in FIG. 6 and the proposal device 1 are capable of cooperating with each other, the planning unit 14 in the proposal device 1 may be omitted. The plan generation device 9 is a computer device, and includes a planning unit having a function similar to that of the planning unit 14 as a functional unit of an arithmetic device (a processor) 90.

Figure 7:
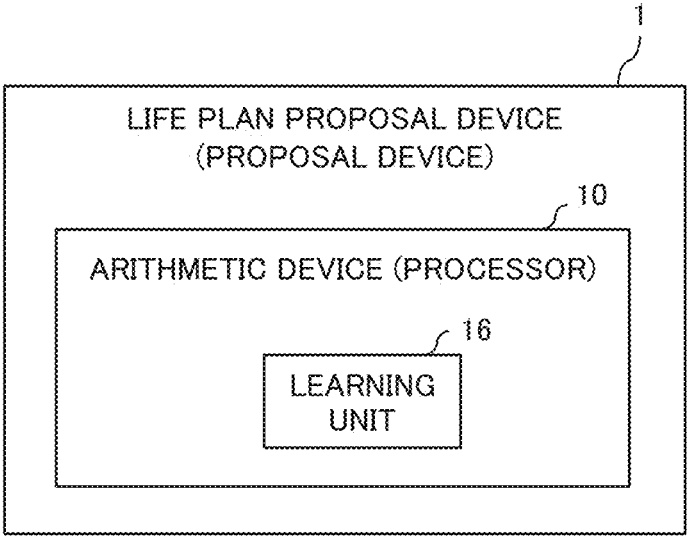
FIG. 7 is a diagram illustrating still another example embodiment of the life plan proposal device.

Furthermore, the proposal device 1 may include a learning unit 16 as illustrated in FIG. 7 as a functional unit of an arithmetic device (a processor) 10. The learning unit 16 accumulates information or learns a model based on an AI technology by a machine learning algorithm in order to improve the accuracy of estimation by the estimation unit 13. The proposal device 1 illustrated in FIG. 7 has the same configuration as the configuration illustrated in FIG. 1, but the functional units such as the acquisition unit 11 and the expansion unit 12 and the storage device 20 are not illustrated.

For example, the estimation result (that is, the estimation result of the occurrence of the life event and the time of the life event) estimated by the estimation unit 13 is transmitted from the proposal device 1 to the terminal device 3 of the user, and correctness/incorrectness information on the estimation result is acquired from the user by using the screen display of the display device 4 of the terminal device 3. The learning unit 16 stores the correctness/incorrectness information indicating the correctness/incorrectness of the estimation result acquired from the user in the storage device 20 in association with the related estimation result. In other words, the learning unit 16 assigns a ground-truth label or a false label to the information of the estimation result by the estimation unit 13 by using the correctness/incorrectness information acquired from the user.

The learning unit 16 generates learning information by associating the estimation result to which the correctness/incorrectness information is given with the living condition information used for the estimation processing from which the estimation result is derived. As learning processing using the learning information, the learning unit 16 adds information on a relationship degree between the life event and the event-relevant term to, for example, relationship data (that is, information relevant to the processing of the estimation unit 13) between the life event and the event-relevant term given in advance. In a case where the estimation unit 13 estimates the occurrence of the life event by the rule-based method, the accuracy of the estimation result by the estimation unit 13 can be enhanced by using the information of the event-relevant term to which such information of the relationship degree is added.

In a case where the estimation unit 13 uses a classification model or a clustering model, the learning unit 16 learns the model used by the estimation unit 13 by a machine learning algorithm, as the learning processing using the learning information generated as described above. As a result, the estimation result by the estimation unit 13 can be enhanced. The model used by the estimation unit 13 can also be said to be information relevant to the processing of the estimation unit 13.

Figure 8:
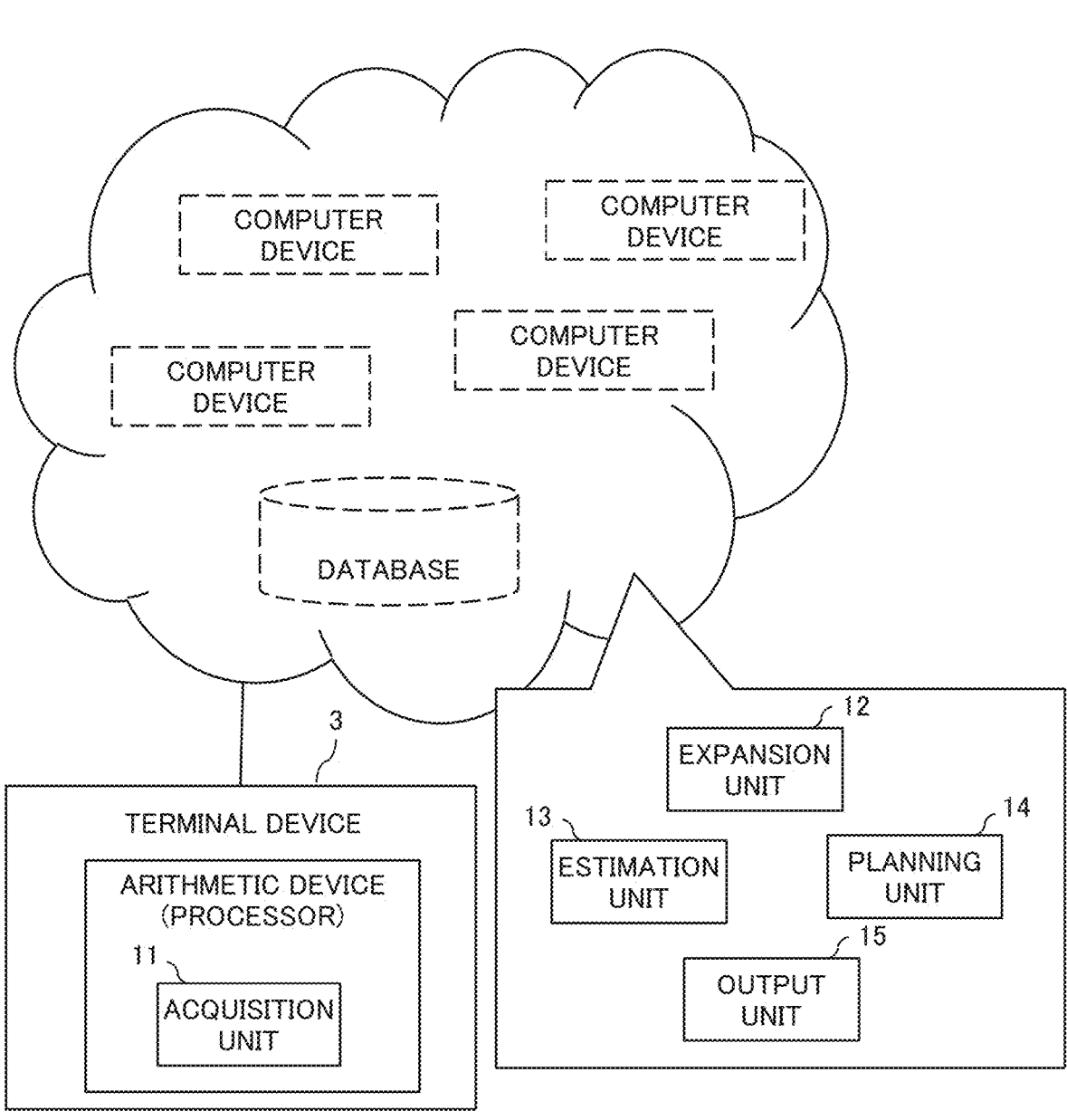
FIG. 8 is a diagram illustrating an example of a life plan proposal system.
Figure 9:
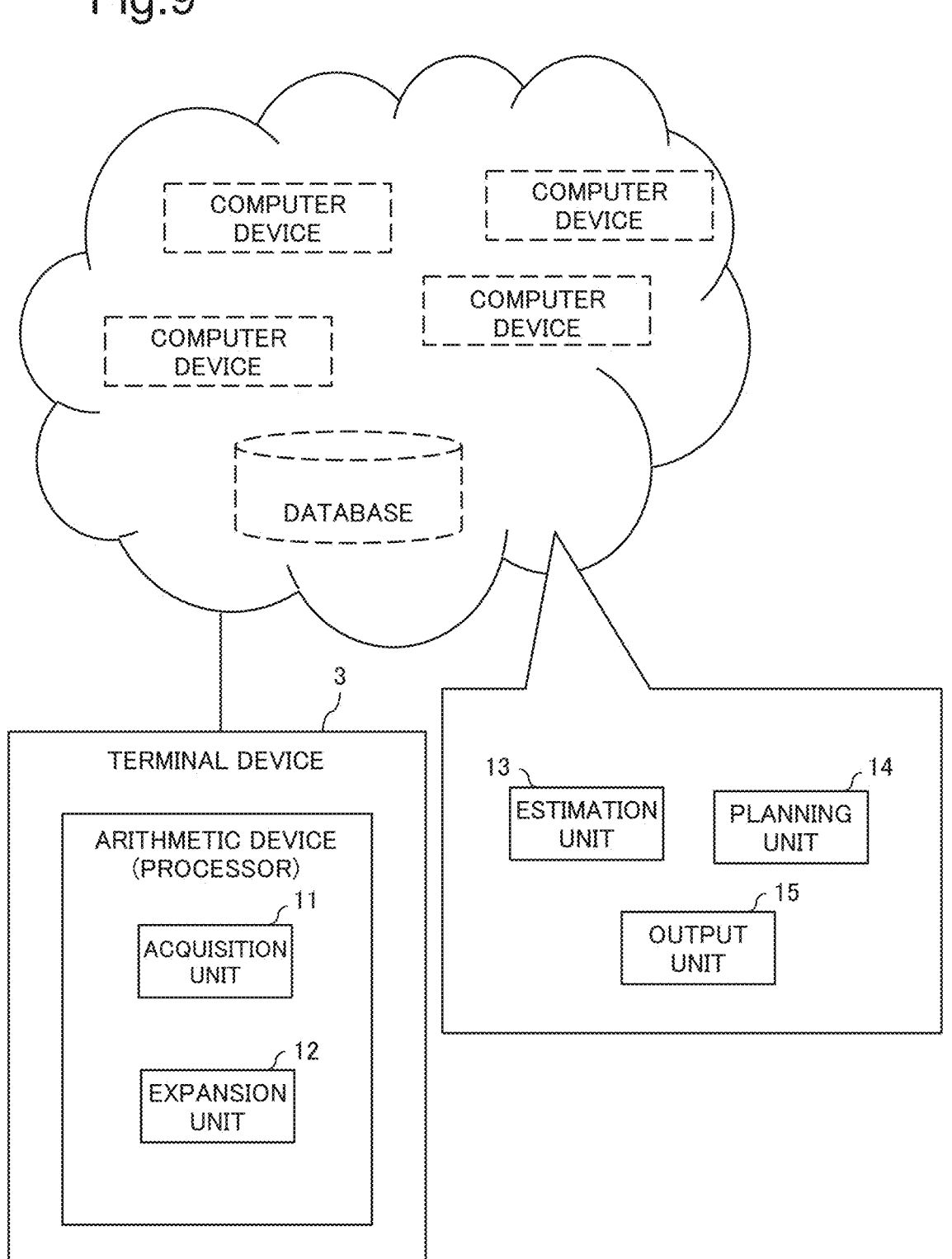
FIG. 9 is a diagram illustrating an example of the life plan proposal system.
Figure 10:
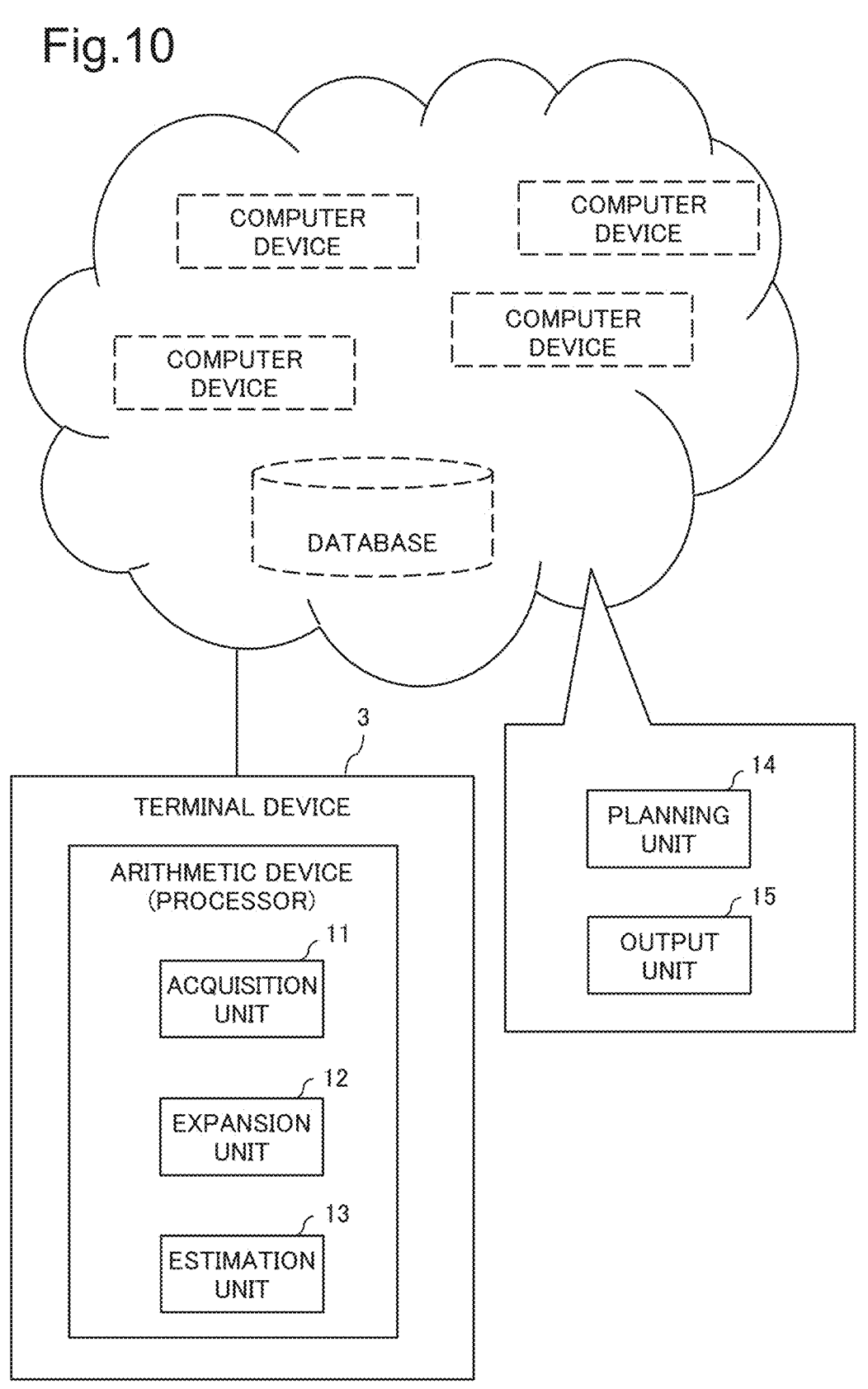
FIG. 10 is a diagram illustrating an example of the life plan proposal system.
Figure 11:
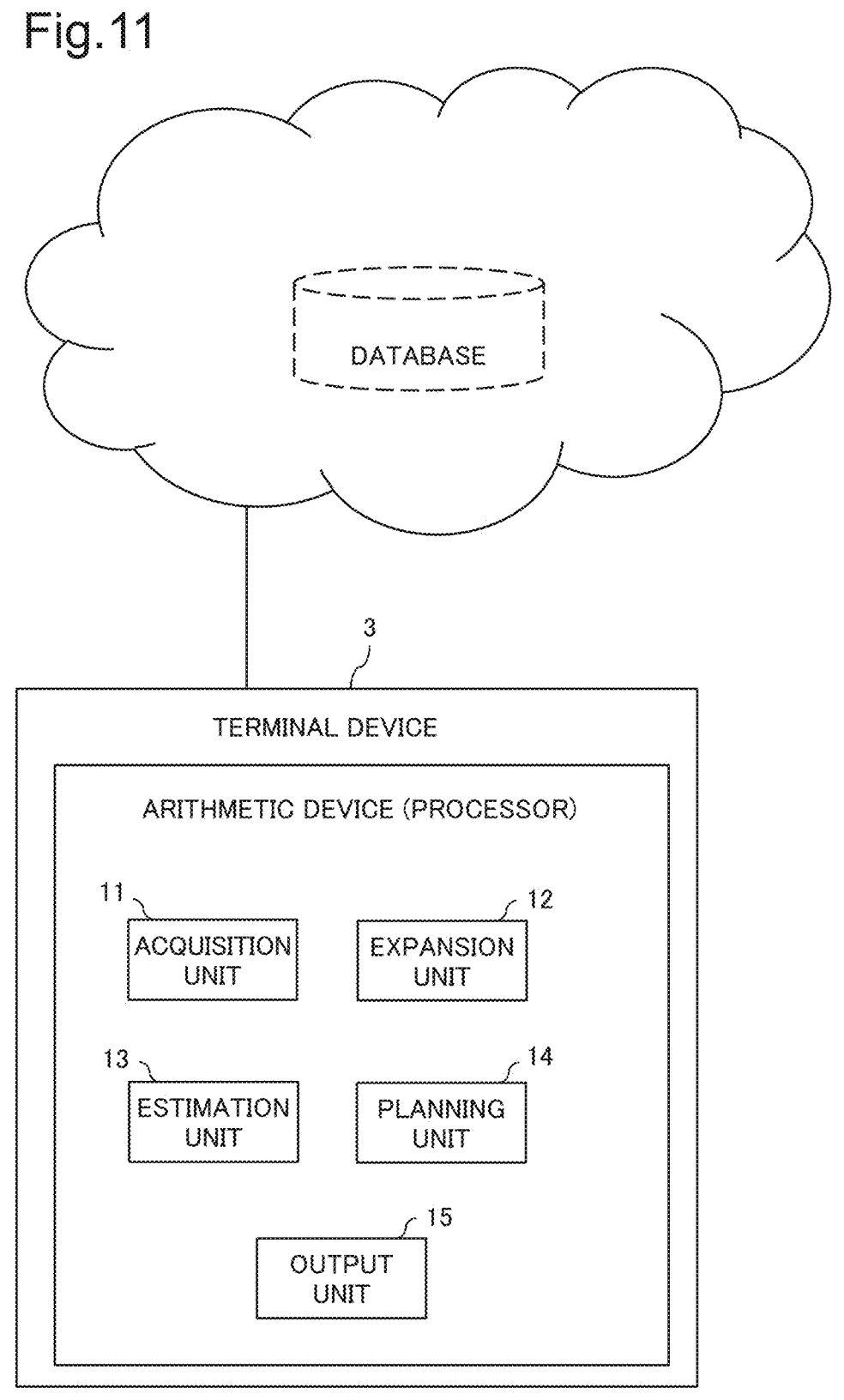

In the first example embodiment, the processing according to the life plan proposal service is mainly executed by the proposal device 1. On the other hand, a plurality of pieces of processing according to the life plan proposal service described in the first example embodiment may be performed in a distributed manner by the cooperation of the plurality of computer devices including the terminal device 3, for example. For example, as illustrated in FIG. 8, the terminal device 3 may have the function of the acquisition unit 11. As illustrated in FIG. 9, the terminal device 3 may have the functions of the acquisition unit 11 and the expansion unit 12. As illustrated in FIG. 10, the terminal device 3 may have the functions of the acquisition unit 11, the expansion unit 12, and the estimation unit 13. As illustrated in FIG. 11, the terminal device 3 may have the functions of the acquisition unit 11, the expansion unit 12, the estimation unit 13, the planning unit 14, and the output unit 15. That is, in this case, the terminal device 3 can also be regarded as the proposal device 1, and the output unit 15 outputs the information of the life plan by performing the display control of the display device 4, for example. As illustrated in FIG. 12, the terminal device 3 may include a functional unit that executes main processing of the processing according to the life plan proposal service, and a functional unit (the acquisition unit 11) that acquires information may be provided on the computer device side (the server side) to which the terminal device 3 is connected through the information communication network.

In the case of performing distributed processing, the processing is not necessarily assigned to the plurality of computer devices in a unit of the functional units such as the acquisition unit 11, the expansion unit 12, and the estimation unit 13 described in the first example embodiment, and the processing may be further divided and assigned to the plurality of computer devices. In such a case, for example, means such as an acquisition means for acquiring the attribute information indicating the user and the living condition information relevant to the living condition of the user, an extension means for adding the additional attribute information of the user by the information generation method using the acquired attribute information, and an estimation means for estimating the life event that is likely to happen in the user's life and the time of the life event by using the attribute information including the added attribute information and the living condition information of the user are configured by the plurality of computer devices.

It can also be said that FIGS. 8 to 12 illustrate configuration examples of an example embodiment of the life plan proposal system in the present disclosure.

Figure 13:
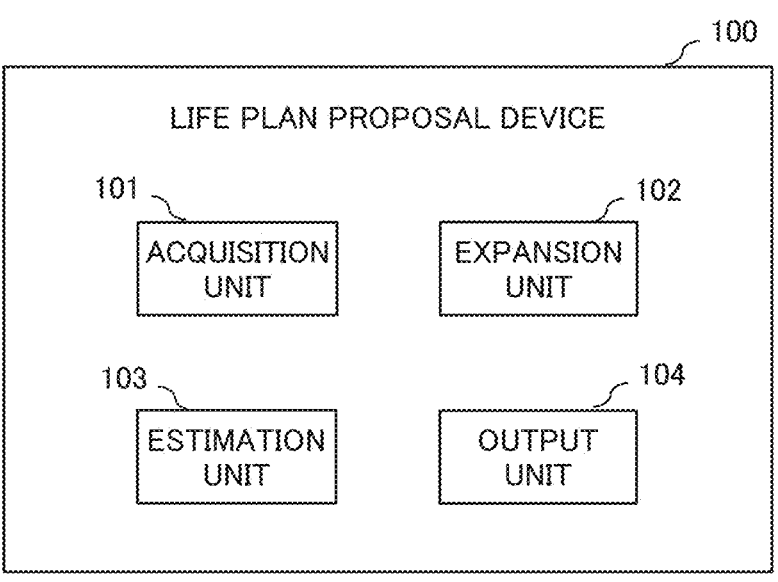
FIG. 13 is a diagram illustrating still another example embodiment of the life plan proposal device.

The life plan proposal device according to the present disclosure may also adopt a configuration as illustrated in FIG. 13. For example, a life plan proposal device 100 illustrated in FIG. 13 is, for example, a computer device, and includes an acquisition unit 101, an expansion unit 102, an estimation unit 103, and an output unit 104 as functional units enabled by executing a computer program. The acquisition unit 101 acquires the attribute information indicating the user and the living condition information relevant to the living condition of the user. The expansion unit 102 adds the additional attribute information of the user by the information generation method using the acquired attribute information. The estimation unit 103 estimates the life event that is likely to happen in the user's life and the time of the life event by using the attribute information including the added attribute information and the living condition information of the user. The output unit 104 outputs the life plan generated by using the information of the estimated life event. The acquisition unit 11, the expansion unit 12, the estimation unit 13, and the output unit 15 described in the first example embodiment are examples of the acquisition unit 101, the expansion unit 102, the estimation unit 103, and the output unit 104

Figure 14:
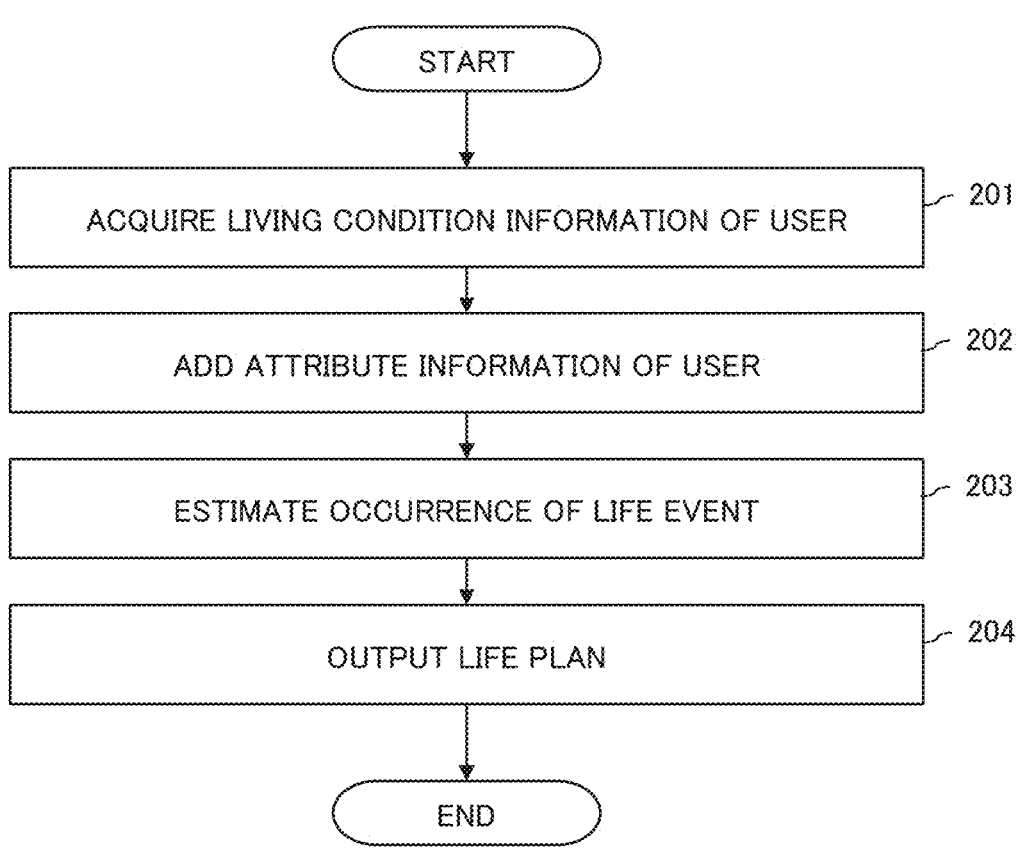
FIG. 14 is a flowchart illustrating another operation example of the life plan proposal device.

The life plan proposal device 100 has the above-described configuration. An example of the operation of the life plan proposal device 100 will be described with reference to FIG. 14. FIG. 14 is a flowchart illustrating an example of the operation of the life plan proposal device 100, and is a diagram illustrating an example of a life plan proposal method by the life plan proposal device 100.

For example, the acquisition unit 101 of the life plan proposal device 100 acquires the attribute information indicating the user and the living condition information relevant to the living condition of the user (step 201). The expansion unit 102 adds the additional attribute information of the user by the information generation method using the attribute information acquired as described above (step 202). The estimation unit 103 estimates the life event that is likely to happen in the user's life and the time of the life event by using the attribute information including the added attribute information and the living condition information of the user (step 203). After that, the output unit 104 outputs the life plan generated by using the information of the estimated life event (step 204).

Since the life plan proposal device 100 has the above-described configuration, it is possible to achieve an effect of enabling a life plan suitable for the current state of the user to be proposed without information from the user.

Some or all of the above example embodiments can be described as in the following supplementary notes, but are not limited to the followings.

Supplementary Note 1

A life plan proposal device, including:
a memory configured to store instructions; and
at least one processor configured to execute the instructions to:
acquire attribute information indicating a user and living condition information relevant to a living condition of the user;
add additional attribute information of the user by an information generation method using the acquired attribute information;
estimate a life event that is likely to happen in the user's life and a time of the life event by using the attribute information including the added attribute information, and the living condition information of the user; and
output a life plan generated by using information of the estimated life event.

Supplementary Note 2

The life plan proposal device according to supplementary note 1,
in which the at least one processor is further configured to execute the instructions to
generate a life plan of the user by using information of the estimated time of the life event.

Supplementary Note 3

The life plan proposal device according to supplementary note 1 or 2, in which the information generation method is a method using a language model that outputs attribute information in response to input of a query including the acquired attribute information.

Supplementary Note 4

The life plan proposal device according to any one of supplementary notes 1 to 3,
in which the at least one processor is further configured to execute the instructions to
execute learning processing of information relevant to processing of the life event and the time of the life event by using information associated with correctness/incorrectness information on information of the estimated life event as learning information.

Supplementary Note 5

The life plan proposal device according to any one of supplementary notes 1 to 4,
in which the at least one processor is further configured to execute the instructions to
acquire a collection of pieces of information including living condition information on a plurality of users, group the living condition information of the plurality of users in the collection of pieces of information by using a clustering technology, and acquire the living condition information of each user by using a feature analyzed for each group.

Supplementary Note 6

The life plan proposal device according to any one of supplementary notes 1 to 5,
in which the at least one processor is further configured to execute the instructions to
acquire information of whether information of the estimated life event is correct from the user.

Supplementary Note 7

The life plan proposal device according to supplementary note 4,
in which the correctness/incorrectness information on the information of the estimated life event is acquired from the user.

Supplementary Note 8

A life plan proposal method, including:
by a computer,
acquiring attribute information indicating a user and living condition information relevant to a living condition of the user;
adding additional attribute information of the user by an information generation method using the acquired attribute information;
estimating a life event that is likely to happen in the user's life and a time of the life event by using the attribute information including the added attribute information, and the living condition information of the user; and
outputting a life plan generated by using information of the estimated life event.

Supplementary Note 9

A non-transitory computer readable program storage medium storing a computer program for causing a computer to execute:

acquiring attribute information indicating a user and living condition information relevant to a living condition of the user;

adding additional attribute information of the user by an information generation method using the acquired attribute information;

estimating a life event that is likely to happen in the user's life and a time of the life event by using the attribute information including the added attribute information, and the living condition information of the user; and outputting a life plan generated by using information of the estimated life event.

Some or all of the configurations described in supplementary notes 2 to 7 dependent on supplementary note 1 described above may also depend on supplementary notes 8 and 9 by the same dependency relationship as supplementary notes 2 to 7. Not limited to supplementary notes 1, 8, and 9, some or all of the configurations described as the supplementary notes can also be similarly dependent on various hardware, software, various recording means for recording software, or systems without departing from the above-described example embodiments.

The previous description of embodiments is provided to enable a person skilled in the art to make and use the present invention. Moreover, various modifications to these example embodiments will be readily apparent to those skilled in the art, and the generic principles and specific examples defined herein may be applied to other embodiments without the use of inventive faculty. Therefore, the present invention is not intended to be limited to the example embodiments described herein but is to be accorded the widest scope as defined by the limitations of the claims and equivalents.

Further, it is noted that the inventor's intent is to retain all equivalents of the claimed invention even if the claims are amended during prosecution.

The invention claimed is:

1. A life plan proposal device, comprising:
a memory configured to store instructions; and
at least one processor configured to execute the instructions to:
acquire correctness/incorrectness information on information of life event from a user;
generate a model by executing machine-learning based on the information of the life event associated with the correctness/incorrectness information;
acquire attribute information indicating a user and living condition information relevant to a living condition of the user;
generate, based on the acquired attribute information, a query by inserting the acquired attribute information into a predetermined query template;
input the generated query to a language model configured to output candidate additional attribute information in response to the generated query;
obtain, from the language model, (i) the candidate additional attribute information and (ii) confidence information indicating an appearance probability associated with each candidate additional attribute information;
select, as additional attribute information of the user, one or more candidates whose confidence information satisfies a predetermined threshold;
store, in association with the user, the selected additional attribute information together with the confidence information;
estimate a life event that is likely to happen in the user's life and a time of the life event by using the generated model, based on the attribute information including the selected additional attribute information, the confidence information, and the living condition information of the user; and
output a life plan generated by using information of the estimated life event.

2. The life plan proposal device according to claim 1, wherein the at least one processor is further configured to execute the instructions to:
generate the life plan of the user by using information of the estimated time of the life event.

3. The life plan proposal device according to claim 1, further comprising an information generation comprising using a language model that outputs attribute information in response to input of a query including the acquired attribute information.

4. The life plan proposal device according to claim 1, wherein the at least one processor is further configured to execute the instructions to:
acquire a collection of pieces of information including the living condition information on a plurality of users, group the living condition information of the plurality of users in the collection of pieces of information by using a clustering technology, and acquire the living condition information of each user by using a feature analyzed for each group.

5. The life plan proposal device according to claim 1, wherein the at least one processor is further configured to execute the instructions to:
acquire information of whether information of the estimated life event is correct from the user.

6. A life plan proposal method, comprising:
by a computer:
acquiring correctness/incorrectness information on information of life event from a user;
generating a model by executing machine-learning based on the information of the life event associated with the correctness/incorrectness information;
acquiring attribute information indicating a user and living condition information relevant to a living condition of the user;
generating, based on the acquired attribute information, a query by inserting the acquired attribute information into a predetermined query template;
inputting the generated query to a language model configured to output candidate additional attribute information in response to the generated query;
obtaining, from the language model, (i) the candidate additional attribute information and (ii) confidence information indicating an appearance probability associated with each candidate additional attribute information;
selecting, as additional attribute information of the user, one or more candidates whose confidence information satisfies a predetermined threshold;
storing, in association with the user, the selected additional attribute information together with the confidence information;
estimating the life event that is likely to happen in the user's life and a time of the life event by using the generated model, based on the attribute information including the selected additional attribute information, the confidence information, and the living condition information of the user; and
outputting a life plan generated by using information of the estimated life event.

7. A non-transitory computer readable program storage medium storing a computer program for causing a computer to execute:

acquiring correctness/incorrectness information on information of life event from a user;

generating a model by executing machine-learning based on the information of the life event associated with the correctness/incorrectness information;

acquiring attribute information indicating a user and living condition information relevant to a living condition of the user;

generating, based on the acquired attribute information, a query by inserting the acquired attribute information into a predetermined query template;

inputting the generated query to a language model configured to output candidate additional attribute information in response to the generated query;

obtaining, from the language model, (i) the candidate additional attribute information and (ii) confidence information indicating an appearance probability associated with each candidate additional attribute information;

selecting, as additional attribute information of the user, one or more candidates whose confidence information satisfies a predetermined threshold;

storing, in association with the user, the selected additional attribute information together with the confidence information;

estimating the life event that is likely to happen in the user's life and a time of the life event by using the generated model, based on the attribute information including the selected additional attribute information, the confidence information, and the living condition information of the user; and outputting a life plan generated by using information of the estimated life event.

8. The life plan proposal device according to claim 1, wherein the at least one processor is further configured to execute the instructions to:

update the life plan at predetermined timing;

output the updated life plan in a case where an updated life plan provision request is acquired.

* * * * *